Figure 1:
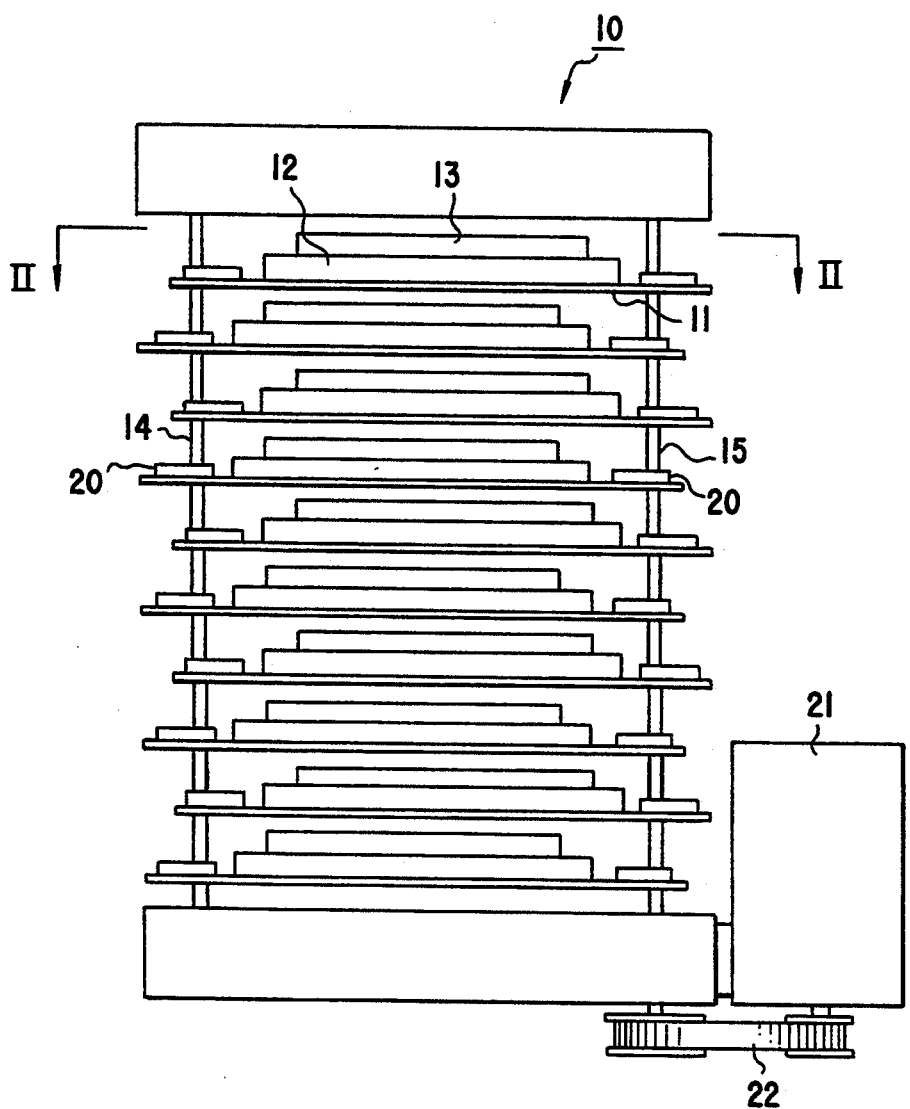

United States Patent [19]

Heinonen et al.

[11] Patent Number: 5,346,303
[45] Date of Patent: Sep. 13, 1994

[54] SHAKER/INCUBATOR

[75] Inventors: Aarne Heinonen; Hannu Hietanen, both of Turku, Finland

[73] Assignee: Wallac Oy, Turku, Finland

[21] Appl. No.: 55,298

[22] Filed: May 3, 1993

[30] Foreign Application Priority Data

May 4, 1992 [FI] Finland .................................. 922003

[51] Int. Cl.[5] .............................................. B01F 11/00
[52] U.S. Cl. ...................................... 366/208; 366/219
[58] Field of Search ............... 366/208, 209, 217, 219, 366/235, 210, 211, 213, 216, 237, 53

[56] References Cited

U.S. PATENT DOCUMENTS

| | | | |
|---|---|---|---|
| 4,673,297 | 6/1987 | Siczek | 366/208 |
| 4,747,693 | 5/1988 | Kahl | 366/208 |
| 4,750,845 | 6/1988 | Nabetani | 366/219 |

Primary Examiner—Robert W. Jenkins
Attorney, Agent, or Firm—Adduci, Mastriani, Schaumberg & Schill

[57] ABSTRACT

A shaker/incubator (10) comprising an even number of shaking planes (11) placed one on top of the other, which can be brought into a shaking motion by means of a rotating shaft (15) with eccentrics (20) attached thereto. Every second shaking plane is in the same phase of the shaking motion. The shaking planes are connected to each other by three vertical shafts (14, 15, 16) or by one vertical shaft (15) disposed in the middle so that the shaking plane connected to a toothed gear (24) rolls along a toothed rim (26) formed in the body (25).

3 Claims, 3 Drawing Sheets

SHAKER/INCUBATOR

The invention relates to a shaker/incubator comprising a shaking plane or other member, which the samples to be shaken can be placed in contact with and which is brought into a shaking motion by a rotating shaft with an attached eccentric or a corresponding apparatus.

Known shaker/incubators are usually planes which are brought into shaking motion by a rotating eccentric shaft mounted in the middle of the plane. Rotation of the shaker/incubator plate round the eccentric shaft is prevented by springs on the edges of the plate supporting the plate on the body. The apparatus is used so that the samples to be shaken are placed on the plate side by side.

The drawback with known shaker/incubators is that the vibrating motion caused by the eccentric shaft is as desired only in the middle of the plate. Forced shaking motion occurs only near the rotating eccentric shaft. At the edges of the plate the springs supporting the plate on the body yield and there the shaking motion can be completely different. Since different parts of the shaking plate perform different shaking motions, the samples will not be shaken uniformly and mutually in the same way. The situation is even worse if the plate is loaded in an unbalanced way.

Another drawback with known shaker/incubators is that one plate can accommodate only a small number of samples. Known shaking mechanisms do not permit several plates to be placed one on top of the other because the shaking forces might become uncontrollably high and the whole apparatus might get out of balance.

The apparatus according to the invention is characterized in that the shaker/incubator comprises two or more shaking planes or corresponding members placed one on top of the other, the shaking motion of which is obtained so that the shaking planes are supported by two or more mechanical supports at least one of which is the rotating shaft with the attached eccentric.

According to the invention one thus obtains two shaking planes placed one on top of the other, which are connected to the same shaft by means of eccentrics so that the shaking planes are all the time in opposite phases of the shaking motion.

According to one advantageous embodiment, the shaking planes of the shaker/incubator are connected to each other by means of three vertical shafts, which are situated at different edges of the shaking plane so that the shafts are situated, as seen from above, at apices of a triangle. One shaft is rotated by an electric motor whereupon the other shafts with the eccentrics are in the same phase of their rotational motions or on the same side of the shafts.

According to another advantageous embodiment a vertical shaft with an attached eccentric is disposed in the middle of the shaker/incubator, to which eccentric the shaking plane is mounted by means of a bearing. A toothed gear concentric with the bearing is connected to the shaking plane, the toothed gear being fitted to roll along a toothed rim formed in the body of the shaker/incubator. The difference between the diameter of the toothed rim and that of the toothed gear is twice as large as the distance between the centre of the eccentric and that of the shaft.

The distance between the centre of the eccentric and that of the shaft i.e. the eccentricity is advantageously 1 mm+/−0,5 mm and the difference between the diameter of the toothed rim and that of the toothed gear is 2 mm+/−1 mm. In this case the diameter of the toothed gear is, for example, about 100 mm. The location of each recess of the slowly revolving shaking plane can be determined on the basis of the number of revolutions of the shaft. The shaker/incubator has 10 shaking planes placed one on top of the other and each shaking plane has 10 radial recesses.

Figure 2:
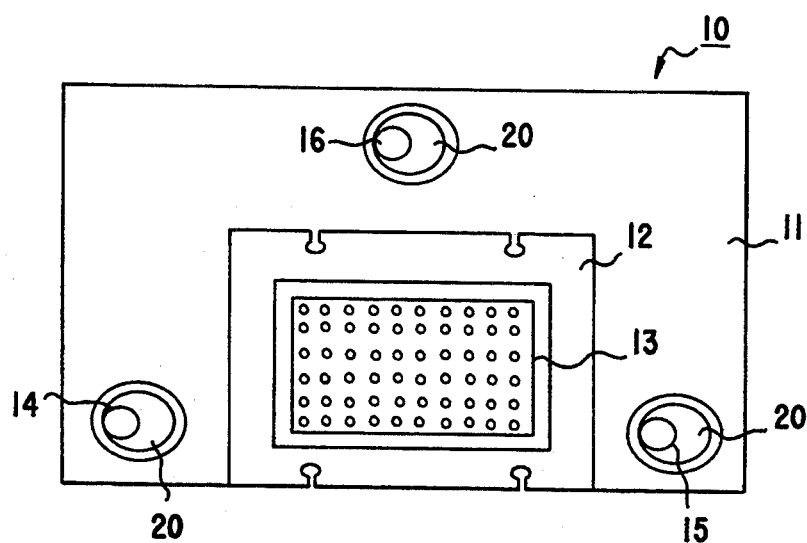
Figure 3:
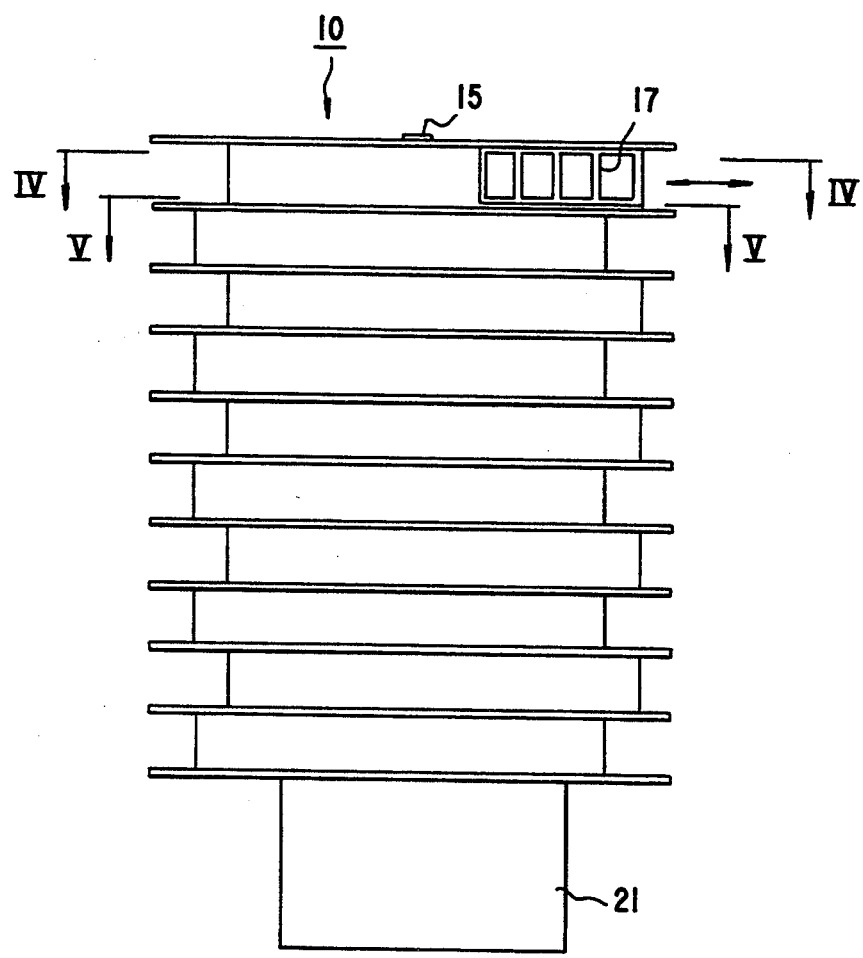
Figure 4:
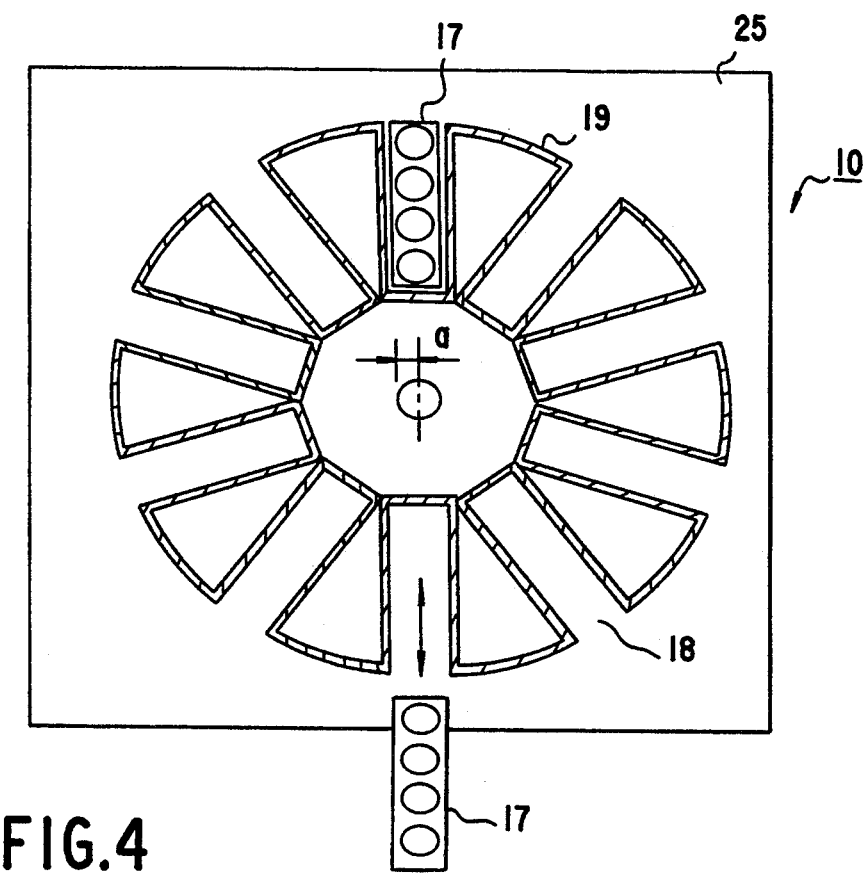
Figure 5:
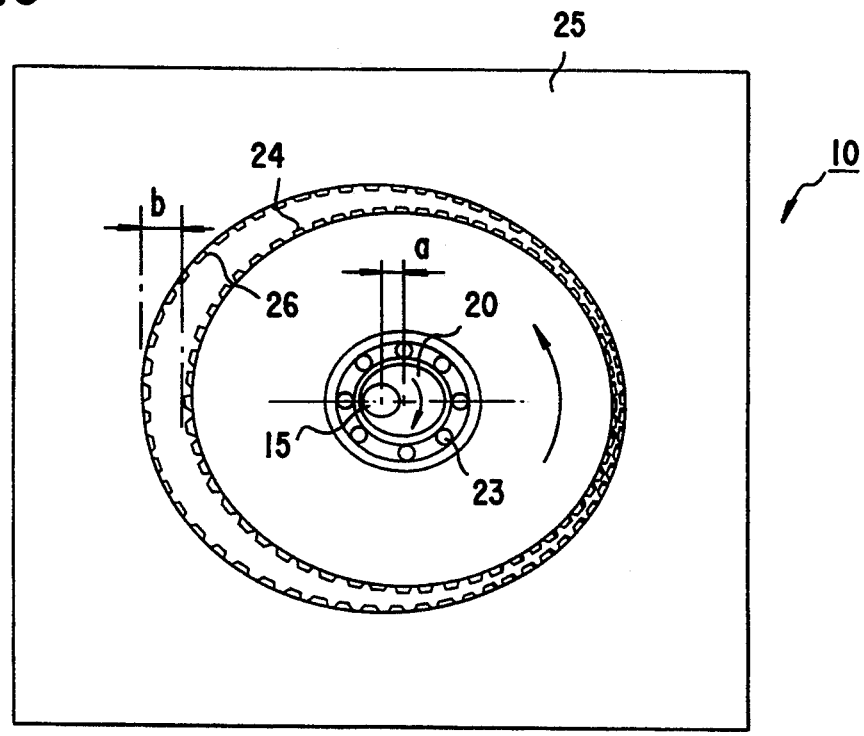

The invention will be explained in greater detail in the following referring to the enclosed drawings in which FIG. 1 shows a shaker/incubator according to the invention seen from the side, FIG. 2 shows the cross-section along the line II—II in FIG. 1, FIG. 3 corresponds to FIG. 1 and shows another embodiment of a shaker/incubator seen from the side, FIG. 4 shows the cross-section along the line IV—IV in FIG. 3, and FIG. 5 shows the cross-section along the line V—V in FIG. 3.

FIG. 1 shows a side view of a shaker/incubator 10 according to the invention. The apparatus comprises 10 planes 11 placed one on top of the other onto which sample plates 13 in frames 12 are placed for shaking and incubation of the samples. Planes 11 are connected to each other through shafts and eccentrics connected to the shafts. There are three shafts, but FIG. 1 shows only the two shafts 14 and 15 in the front and the eccentrics 20 which are connected to planes 11 through bearings.

The shaking motion of the planes 11 and the sample plates 13 thereon is obtained so that an electric motor 21 rotates the shaft 15 with eccentrics 20 by a toothed belt 22. Because the shaft 14 and the other shaft at the rear of the shaking apparatus 10 are connected with the rotated shaft 15 through planes 11, all planes 11 are brought into a horizontal shaking motion determined by the eccentrics 20.

FIG. 1 also shows that the eccentrics 20 of the planes 11 are connected to the shafts 14 and 15 so that the shaking motion of planes which are situated on top of the other are in opposite phases. In other words, when a plane 11 of the shaking apparatus 10 is situated at one edge of the apparatus, the closest plane 11 is situated at the opposite edge.

FIG. 2 shows a cross-section of FIG. 1 showing one plane 11 of the shaker/incubator from above. FIG. 2 shows that a sample plate 13 with its frame 12 has been placed on the plane 11. The plate 11 has been connected to the shaker/incubator 10 with three shafts 14, 15, and 16 on different sides of the plate 11. Every shaft has attached eccentrics 20 which are situated on the same side of the shafts i.e. on the right side in FIG. 2. Now, on rotating the shaft 15 by an electric motor 21, the shaft arrangement of the figure causes a simultaneous rotation of the shafts 14 and 16 as well. The eccentrics 20 also are then always situated on the same side of the shafts. Therefore, each point of the plate 11 is in a similar shaking motion. The shaker/incubator as a whole is, however, balanced because the two plates 11 arranged one on top of the other are always in opposite phases relative to each other.

FIG. 3 shows a second embodiment of the shaker/incubator according to the invention wherein the electric motor 21 rotates only one shaft 15. This apparatus is not intended for sample plates 13 as was the apparatus of FIGS. 1 and 2, but for sample bars 17. This apparatus is intended to shake sample bars 17, which contain small amounts of sample and which are fed into the apparatus from the side. Structure of the apparatus of FIG. 3 and its operating principle is shown in more details in FIGS. 4 and 5. It is similar with the apparatus presented in the previous figures in that the samples to be shaken are placed into the apparatus in layers and that two closest layers are always in opposite shaking phases. FIG. 4 shows a cross-section of the shaker/incubator of FIG. 3. The figure shows that the sample bars 17 are fed into the corresponding recesses 18 of the shaker/incubator 10 in radial direction.

FIG. 5 shows the operating principle of the shaker/incubator 10 of FIG. 3. Shaft 15, which is rotated by the electric motor 21, has an attached eccentric 20 which is in contact with a toothed gear 24 through a bearing 23. When the shaft 15 is rotating, the eccentric 20 rolls the toothed gear 24 against the toothed rim 26 formed in the body 25. Since the number of teeth in the toothed gear 24 is less than that of the toothed rim 26, the toothed gear 24 on rolling gets into a rotating motion which is opposite in direction to the rotational motion of the shaft 15 and the eccentric attached thereto. This is exploited in the shaker/incubator so that the toothed gear 24, which is brought into both a shaking and a rotating motion, is connected to a holder 19 of sample bars 17 shown in FIG. 4. This arrangement brings along an advantage in that, when the sample bars 17 are shaken, they slowly rotate round the shaker. Then it is possible to determine, from the number of rotations of the shaft 15, the time when some sample bar 17 is at a suitable location for removing from the holder 19 or feeding a new bar 17 into the holder 19.

In FIG. 5, the dimensions of the diameters of the toothed rim 26 and the toothed gear 24 are exaggerated for clarity. The distance (a) between the centre of the eccentric 20 and that of the shaft 15 is fairly large in the drawing but in reality this eccentricity is only 1 mm+/−0,5 mm. Because the difference (b) between the diameter of the toothed rim 26 and that of the toothed gear 24 is twice as large as the distance (a) between the centre of the eccentric 20 and that of the shaft 15, the measure (b) is in reality only 2 mm+/−1 mm. The diameter of the toothed gear 24 is about 100 mm, for example.

It is obvious to a specialist in the field that different embodiments of the invention may vary within the limits of the enclosed claims.

We claim:

1. A shaker comprising at least two shaking plates, each plate having a plurality of recesses; a plurality of shaking bars, including an amount of a sample, insertable and removable from said plurality of recesses; a vertical separation distance defined between said at least two plates; a rotatable shaft connected to said at least two plates by an eccentric; drive means for driving said shaft and said eccentric in a predetermined rotational direction; a first gear connected to said eccentric; a second gear provided on a portion of said at least two shaking plates; sections of said first and second gears in rolling contact with each other; said first gear having a predetermined number of teeth which is less than a predetermined number of teeth of said second gear; said first gear rotating in a direction opposite to said predetermined rotational direction of said shaft and said eccentric and said first gear concentric with said eccentric; and, a predetermined difference established between diameters of said first and said second gears in which the diameter of the first gear is substantially twice as large as a distance established between a center point of said eccentric and a center point of said shaft.

2. A shaker according to claim 1 wherein said distance is in a range of 0.5 to 1.50 mm; and said difference is in a range of 1 mm to 3 mm.

3. A shaker according to claim 1, wherein each of said at least two shaking plates has at least 10 recesses and said recesses are radially located in said at least two shaking plates.

* * * * *